US005510059A

United States Patent [19]
Yuki et al.

[11] Patent Number: 5,510,059
[45] Date of Patent: Apr. 23, 1996

[54] SURFACE-TREATED MELAMINE CYANURATE POWDER AND PROCESS FOR ITS PRODUCTION

[75] Inventors: Shinichi Yuki, Tokyo; Kouji Shishido; Masayoshi Shirakawa, both of Toyama; Masuo Shindo, Funabashi, all of Japan

[73] Assignee: Nissan Chemical Industries, Ltd., Tokyo, Japan

[21] Appl. No.: 377,341

[22] Filed: Jan. 24, 1995

[30] Foreign Application Priority Data

Feb. 8, 1994 [JP] Japan .................... 6-014380

[51] Int. Cl.$^6$ .................... C09K 21/00; C09K 15/22
[52] U.S. Cl. .................... 252/609; 252/403; 529/409
[58] Field of Search .................... 252/609, 403; 524/409

[56] References Cited

U.S. PATENT DOCUMENTS 4,387,224  6/1983  Fromm et al. .................... 544/201

OTHER PUBLICATIONS

Patent Abstracts of Japan, vol. 18, No. 122 (C–1173), Feb. 28, 1994, JP–5–310716, Nov. 22, 1993.

Patent Abstracts of Japan, vol. 3, No. 79 (C–51), Jul. 6, 1979, JP–54–55588, Feb. 5, 1979.

Patent Abstracts of Japan, vol. 5, No. 20 (C–42) (692), Feb. 6, 1981, JP–147266, Nov. 17, 1980.

Patent Abstracts of Japan, vol. 8, No. 67 (C–216) (1504), Mar. 29, 1984, JP–58–222073, Dec. 23, 1983.

*Primary Examiner*—Kriellion S. Morgan
*Attorney, Agent, or Firm*—Oblon, Spivak, McClelland, Maier & Neustadt

[57] ABSTRACT

A melamine cyanurate powder composed of readily dispersible aggregated primary particles of melamine cyanurate surface-treated with a metal oxide.

8 Claims, No Drawings

SURFACE-TREATED MELAMINE CYANURATE POWDER AND PROCESS FOR ITS PRODUCTION

The present invention relates to a melamine cyanurate powder surface-treated with a metal oxide and a process for its production. The melamine cyanurate powder of the present invention is useful as an additive to a lubricant or as a flame retardant for a synthetic resin.

As a method for producing melamine cyanurate, a neutralization reaction which comprises mixing an aqueous melamine solution with an aqueous cyanuric acid solution to precipitate melamine cyanurate (Japanese Examined Patent Publication No. 5595/1970) or a heterogeneous neutralization reaction of a solid dispersion of melamine and cyanuric acid in water (Japanese Examined Patent Publication No. 34430/1986) is known.

Further, Japanese Unexamined Patent Publication No. 310716/1993 discloses that when melamine cyanurate is produced in the presence of a polyvinyl alcohol and/or a cellulose ether, it is possible to obtain a melamine cyanurate surface-treated by such a material, which has a large bulk density and is excellent in the dispersibility to a resin. However, with a matrix resin which requires a molding temperature of at least 300° C., there has been a problem that the resin undergoes a color change, since the heat resistance of such a surface-treating agent is relatively low.

The present invention has been accomplished as a result of an extensive research with an aim to obtain a melamine cyanurate powder which is weakly aggregated to such an extent that when mixed with a various matrix, it can be finely dispersed to a level of fine particles and which is a powder having fine particles weakly aggregated and having a large bulk density so that from the viewpoint of handling efficiency, it is less dusting by virtue of the weakly aggregated form of melamine cyanurate, by using a surface treating agent having excellent heat resistance.

Namely, the present invention provides a melamine cyanurate powder composed of readily dispersible aggregated primary particles of melamine cyanurate surface-treated with a metal oxide.

Further, the present invention provides a process for producing a melamine cyanurate powder, which comprises reacting melamine with cyanuric acid in an aqueous medium in the presence of a metal oxide sol, and spray drying the resulting aqueous dispersion slurry of melamine cyanurate.

The melamine cyanurate powder of the present invention is characterized in that it takes such a form that primary particles surface-treated with a metal oxide are aggregated. Here, numerous fine particles are aggregated to form individual particles of the melamine cyanurate powder. Such fine particles are referred to as primary particles. Further, to fix a metal oxide to such primary particles is referred to as surface treatment. The process for its production is characterized in that melamine and cyanuric acid is reacted in an aqueous medium in the presence of a metal oxide sol, and the resulting aqueous dispersion slurry of melamine cyanurate is spray-dried.

Now, the present invention will be described in detail with reference to the preferred embodiments.

For the melamine powder as the starting material of the present invention, a commercial product having an average particle size of from 10 to 100 μm can be used as it is. Likewise, for the cyanuric acid powder as another starting material of the present invention, a commercial product having an average particle size of from 10 to 100 μm can be used as it is. The enol form is called cyanuric acid, and the keto form is called isocyanuric acid. However, they are tautomers. For the purpose of the present invention, both the enol form and the keto form will generally be referred to as cyanuric acid.

In the neutralization reaction for forming melamine cyanurate, melamine and cyanuric acid react in equimolar amounts in the presence of water. However, the molar ratio of the melamine to cyanuric acid may not strictly be 1:1, and either melamine or cyanuric acid may be excessive, so long as there will be no problem in the use of the resulting melamine cyanurate. The amount of water required for this reaction is not particularly limited in the present invention, but is usually from 400 to 1000 parts by weight, per 100 parts by weight of the total amount of melamine and cyanuric acid.

As the metal oxide sol to be used in the present invention, various hydrosols or organosols of e.g. silica, alumina, antimony oxide, titania, tin oxide or zirconia, may be mentioned. A preferred sol is a hydrosol of silica, alumina or antimony oxide having a particle size of from a few nm to a few tens nm. The concentration of the metal oxide in the sol is usually from 10 to 30 wt %. In some cases, however, it can be used as diluted or concentrated. The amount of the metal oxide sol is usually from 0.1 to 10 parts by weight, preferably from 0.3 to 8 parts by weight, more preferably from 0.5 to 5 parts by weight, as calculated as the metal oxide, per 100 parts by weight of melamine cyanurate. Such a metal oxide sol may be dispersed in the aqueous medium together with melamine and cyanuric acid from the very beginning of the reaction, or may be dispersed during the reaction, or after completion of the reaction and prior to the spray drying. However, it is simple and effective to add the metal oxide sol from the very beginning of the reaction.

The neutralization reaction is carried out usually under atmospheric pressure at a temperature of from room temperature to 100° C. with stirring, but from the viewpoint of the reaction rate, etc., it is preferably carried out at a temperature of from 50° to 100° C., more preferably from 70° to 100° C. The reaction time is usually within a range of from 1 to 2 hours. The aqueous dispersion slurry of melamine cyanurate thus obtained is dried by a usual spray dryer to obtain a melamine cyanurate powder having an average particle size of from a few tens to hundred μm, wherein numerous primary particles having a particle size of from about 0.3 to 3 μm and having the metal oxide fixed thereto, are aggregated.

The metal oxide sol used in the present invention will be fixed as fine particles of the metal oxide on the surface of primary particles of melamine cyanurate at the time of drying. At that time, the fine particles of the metal oxide serve as a weak binder for the primary particles to form a melamine cyanurate powder having a large bulk density. At the same time, the primary particles themselves will electrostatically repel one another since the fine particles of the metal oxide fixed on the primary particles have the same electrical charge, for example, silica or antimony oxide has a negative charge, and alumina has a positive charge. It is believed that in such a manner, a melamine cyanurate powder having primary particles weakly aggregated to such an extent that it can finely be dispersed in matrix, can be formed. Further, it is considered that the melamine cyanurate powder particles themselves will electrostatically repel to one another. Needless to say, the metal oxide is an inorganic substance and inherently heat resistant. Accordingly, the melamine cyanurate powder surface-treated with the metal oxide will also have excellent heat resistance.

As the amount of the metal oxide increases from 5 to 8 and 10 parts by weight, as calculated as the metal oxide, per 100 parts by weight of melamine cyanurate, the degree for improvement of the properties such as the bulk density of the melamine cyanurate powder gradually decreases, and if the amount exceeds 10 parts by weight, a problem will result such that free metal oxide will be present which is not fixed on the surface of primary particles. If the amount of the metal oxide decreases from 0.5 to 0.3 and 0.1 part by weight, as calculated as the metal oxide, per 100 parts by weight of melamine cyanurate, the effect of surface treatment of the primary particles of melamine cyanurate tends to decrease.

Now, the present invention will be described in further detail with reference to Examples, Comparative Examples and Reference Examples. However, it should be understood that the present invention is by no means restricted by such specific Examples.

EXAMPLE 1

Into a reactor equipped with a stirrer, a thermometer and a condenser, 900 kg of water, 7.0 kg of silica hydrosol ($SiO_2$ concentration: 14.4%, $Al_2O_3$ concentration: 0.57%, particle size: 5 nm), 50 kg of a melamine powder having an average particle size of 40 μm and a specific surface area of 0.8 $m^2/g$ and 51.2 kg of a cyanuric acid powder having an average particle size of 50 μm and a specific surface area of 0.6 $m^2/g$ were introduced with stirring and then mixed under heating at 85° C. for 2 hours to obtain an aqueous dispersion slurry having a slurry viscosity of 1300 mPa.s. Then, the slurry was dried by a spray dryer manufactured by Ashizawa Niro Atomizer K.K. at an inlet temperature of 270° C. to obtain a melamine cyanurate powder having a bulk density of 0.38.

EXAMPLE 2

A melamine cyanurate powder was obtained in the same manner as in Example 1 except that instead of the silica hydrosol in Example 1, 5.0 kg of alumina sol 510 (manufactured by Nissan Chemical Industries, Ltd., $Al_2O_3$ concentration: 20.9%, particle size: 10 to 20 nm, pH: 4.03) was used. The slurry viscosity was 1340 mPa·s, and the bulk density of the melamine cyanurate powder was 0.25.

EXAMPLE 3

A melamine cyanurate powder was obtained in the same manner as in Example 1 except that as other silica hydrosol than the one used in Example 1, 5.0 kg of Snowtex C (manufactured by Nissan Chemical Industries, Ltd., $SiO_2$ concentration: 20 to 21%, particle size: 10 to 20 nm) was used. The slurry viscosity was 960 mPa.s, and the bulk density of the melamine cyanurate powder was 0.28.

EXAMPLE 4

A melamine cyanurate powder was obtained in the same manner as in Example 1 except that instead of the silica hydrosol used in Example 1, 7.0 kg of antimony oxide sol A-1510N (manufactured by Nissan Chemical Industries, Ltd., $Sb_2O_5$ concentration: 13%, particle size: 50 nm) was used and the amount of water was changed from 900 kg to 620 kg. The slurry viscosity was 1720 mPa.s, and the bulk density of the melamine cyanurate powder was 0.38.

Comparative Example 1

A melamine cyanurate powder was obtained in the same manner as in Example 1 except that no metal oxide hydrosol was added. The slurry viscosity was 1250 mPa.s, and the bulk density of the melamine cyanurate powder was as low as 0.18, and the powder flowability was poor, and dusting was remarkable.

Reference Example 1

With respect to the melamine cyanurate powders obtained in Examples 1 to 4 and Comparative Example 1, to see the heat resistance of the powders themselves, they were left to stand at 400° C. for 10 minutes, whereupon coloring was visually inspected and compared.

Then, 8 parts by weight of each melamine cyanurate powder was added to 100 parts by weight of nylon 6 (Amilan CM-1007, manufactured by Toray Corporation), and the mixture was kneaded by a twin screw extruder at 230° C. and cooled with water to obtain a compound. The compound was subjected to vacuum drying at 80° C. for 10 hours, and then a test specimen was prepared by an injection molding machine, whereby the flame retardancy (thickness of the test specimen: 3.2 mm) in accordance with UL-94 and the elongation at breakage in a tensile test (23° C.) in accordance with ASTM D638 were measured. Further, the compound was sandwiched between slide glass plates and subjected to heat compression at 260° C., whereupon the dispersed state was inspected and compared by an optical microscope. These results are shown in Table 1.

From Table 1, it should be understood that the melamine cyanurate of the present invention is excellent in the elongation and comparable to Comparative Example 1 with respect to the heat resistance and the flame retardancy. The melamine cyanurate composed of surface-treated primary particles is believed to be a reflection such that it is finely dispersed to a level of primary particles. This is also supported from the results of inspection of the dispersed state in the resin.

TABLE 1

| Test items | Example 1 | Example 2 | Example 3 | Example 4 | Comparative Example 1 |
|---|---|---|---|---|---|
| Heat resistance of powder (Color change) | No change | No change | No change | No change | No change |
| Flame retardancy | V-0 | V-0 | V-0 | V-0 | V-0 |
| Elongation (%) | 28.9 | 26.9 | 32.8 | 30.0 | 18.1 |
| Dispersed state | Good | Good | Good | Good | Aggregated particles present |

The melamine cyanurate powder of the present invention consisting essentially of primary particles surface-treated with a metal oxide, is excellent in the heat resistance, has a large bulk density and is excellent in the flowability without agglomeration of the powder particles. When it is dispersed to a matrix of a resin or a lubricant, it is finely dispersed to a level of primary particles, whereby the mechanical properties of the matrix will be excellent. Yet, the process for its production is simple, as it requires only to mix a small amount of a metal oxide sol at the time of the reaction.

What is claimed is:

1. A melamine cyanurate powder comprising readily dispersible aggregated primary particles of melamine cyanurate, and particles of metal oxide fixed on the surface of said primary particles of melamine cyanurate.

2. The melamine cyanurate powder according to claim 1, wherein the metal oxide is silica, alumina or antimony oxide.

3. The melamine cyanurate powder according to claim 1, wherein the metal oxide is present in an amount of from 0.1 to 10 parts by weight per 100 parts by weight of the melamine cyanurate.

4. The melamine cyanurate powder according to claim 2, wherein the metal oxide is present in an amount of from 0.1 to 10 parts by weight per 100 parts by weight of the melamine cyanurate.

5. A process for producing a melamine cyanurate powder, which comprises reacting melamine with cyanuric acid in an aqueous medium in the presence of a metal oxide sol, and spray drying the resulting aqueous dispersion slurry of melamine cyanurate.

6. The process for producing a melamine cyanurate powder according to claim 5, wherein the metal oxide sol is silica sol, alumina sol or antimony oxide sol.

7. The process for producing a melamine cyanurate powder according to claim 5, wherein the metal oxide sol is present in an amount of from 0.1 to 10 parts by weight as calculated as the metal oxide per 100 parts by weight of the total amount of melamine and cyanuric acid.

8. The process for producing a melamine cyanurate powder according to claim 6, wherein the metal oxide sol is present in an amount of from 0.1 to 10 parts by weight as calculated as the metal oxide per 100 parts by weight of the total amount of melamine and cyanuric acid.

* * * * *